United States Patent
Huber et al.

(10) Patent No.: US 10,788,475 B2
(45) Date of Patent: *Sep. 29, 2020

(54) METHOD FOR DETERMINING PROPERTIES OF A HYDROCARBON CONTAINING GAS MIXTURE AND APPARATUS THEREFOR

(71) Applicant: Endress+Hauser Flowtec AG, Reinach (CH)

(72) Inventors: Christof Huber, Bern (CH); Anastasios Badarlis, Birsfelden (CH)

(73) Assignee: Endress+Hauser Flowtec AG, Reinach (CH)

( * ) Notice: Subject to any disclaimer, the term of this patent is extended or adjusted under 35 U.S.C. 154(b) by 209 days.

This patent is subject to a terminal disclaimer.

(21) Appl. No.: 15/768,013

(22) PCT Filed: Sep. 8, 2016

(86) PCT No.: PCT/EP2016/071198
§ 371 (c)(1),
(2) Date: Apr. 13, 2018

(87) PCT Pub. No.: WO2017/063795
PCT Pub. Date: Apr. 20, 2017

(65) Prior Publication Data
US 2018/0306764 A1    Oct. 25, 2018

(30) Foreign Application Priority Data
Oct. 14, 2015    (DE) .................. 10 2015 117 468

(51) Int. Cl.
*G01N 33/22*    (2006.01)
(52) U.S. Cl.
CPC .................. *G01N 33/225* (2013.01)

(58) Field of Classification Search
CPC ....... G01N 33/225; G01N 2291/02818; G01N 2291/02872; G01N 2291/02881
See application file for complete search history.

(56) References Cited

U.S. PATENT DOCUMENTS

| | | | | |
|---|---|---|---|---|
| 3,393,562 | A | * 7/1968 | Breedlove | .............. G01N 25/32 374/37 |
| 4,384,792 | A | * 5/1983 | Sommers | ............... G01N 11/08 374/36 |

(Continued)

FOREIGN PATENT DOCUMENTS

| CN | 1483144 A | 3/2004 |
|---|---|---|
| CN | 1549927 A | 11/2004 |

(Continued)

OTHER PUBLICATIONS

Search Report for German Patent Application No. 10 2015 117 468.5, German Patent Office, dated Jan. 13, 2016, 7 pp.

(Continued)

*Primary Examiner* — Lisa M Caputo
*Assistant Examiner* — Philip L Cotey
(74) *Attorney, Agent, or Firm* — Kelly J. Smith; Endress+Hauser (USA) Holding Inc.

(57) ABSTRACT

A method for determining properties of a hydrocarbon containing gas mixture, especially natural gas or biogas, comprising: allowing the gas mixture to flow through a measuring arrangement; determining a pressure- and temperature dependent viscosity measured value, an associated measured value of temperature and an associated pressure measured value of the flowing gas mixture; ascertaining a first value of a first variable, which characterizes the energy content of the flowing gas mixture, based on viscosity measured value, the associated measured value of temperature, and the associated pressure measured value, wherein the first variable characterizing the energy content is the (Continued)

Wobbe index or the calorific value of the flowing gas mixture, wherein the Wobbe index is preferable.

11 Claims, 7 Drawing Sheets

(56) References Cited

U.S. PATENT DOCUMENTS

| | | | | |
|---|---|---|---|---|
| 4,941,345 | A * | 7/1990 | Altemark | G01N 9/32 73/23.2 |
| 5,201,581 | A * | 4/1993 | Vander Heyden | G01F 1/90 374/36 |
| 5,288,149 | A * | 2/1994 | Meyer | G01N 33/225 374/36 |
| 5,486,107 | A * | 1/1996 | Bonne | G01N 33/2829 374/43 |
| 5,635,626 | A * | 6/1997 | Hammond | G01N 33/225 137/79 |
| 6,178,811 | B1 * | 1/2001 | Bonne | G01N 11/16 73/54.01 |
| 6,446,487 | B1 * | 9/2002 | Van Wesenbeeck | G01N 27/221 73/23.2 |
| 2003/0054306 | A1 * | 3/2003 | Rusche | F24C 3/128 431/12 |
| 2006/0123892 | A1 * | 6/2006 | Brekelmans | G01F 1/6847 73/61.76 |
| 2008/0087070 | A1 * | 4/2008 | Van Putten | G01K 17/00 73/23.2 |
| 2009/0120168 | A1 * | 5/2009 | Harrison | G01N 9/002 73/54.24 |
| 2009/0229351 | A1 * | 9/2009 | Ryser | G01N 33/225 73/54.09 |
| 2011/0282589 | A1 * | 11/2011 | Ermishin | G01N 33/225 702/24 |
| 2013/0138361 | A1 * | 5/2013 | Wheeler | G01N 33/225 702/24 |
| 2016/0138951 | A1 * | 5/2016 | Pretre | G01F 1/66 702/24 |
| 2017/0184531 | A1 * | 6/2017 | Snelders | G01N 27/221 |
| 2017/0241966 | A1 * | 8/2017 | Lotters | G01N 33/0036 |
| 2017/0284919 | A1 * | 10/2017 | Slater | G01N 11/08 |

FOREIGN PATENT DOCUMENTS

| | | |
|---|---|---|
| CN | 101680868 A | 3/2010 |
| CN | 102138066 A | 7/2011 |
| CN | 102259824 A | 11/2011 |
| CN | 102768168 A | 11/2012 |
| CN | 103038634 A | 4/2013 |
| CN | 103328965 A | 9/2013 |
| CN | 103403523 A | 11/2013 |
| CN | 104181074 A | 12/2014 |
| DE | 2928739 B1 | 6/1980 |
| DE | 3623664 A1 | 1/1988 |
| DE | 19918901 C1 | 5/2001 |
| DE | 69523538 T2 | 5/2002 |
| DE | 102014001165 A1 | 6/2015 |
| EP | 0022493 B1 | 3/1984 |
| EP | 1297317 B1 | 3/2009 |
| EP | 2993472 A1 | 3/2016 |
| GB | 2296091 A | 6/1996 |
| WO | 2015074833 A1 | 3/2015 |

OTHER PUBLICATIONS

Search Report for International Patent Application No. PCT/EP2016/071198, WIPO, dated Feb. 11, 2016, 12 pp.
Bonne, Ulrich and Kubisiak, David, Actuation-based microsensors, Institute of Physics Publishing, Nov. 26, 2001, 12 pp.
Rahman Hebibul, et al, Resonant MEMS Viscosity Sensor of Micro Cantilever Beam Structure, Instrument Technique and Sensor, No. 5. pp. 8-10, Mar. 31, 2015.
Ulrich Bonne and David Kubisiak, Actuation-based microsensors, Smart Materials and Structures, No. 10, pp. 1185-1195, Nov. 26, 2001.

* cited by examiner

METHOD FOR DETERMINING PROPERTIES OF A HYDROCARBON CONTAINING GAS MIXTURE AND APPARATUS THEREFOR

CROSS-REFERENCE TO RELATED APPLICATIONS

The present application is related to and claims the priority benefit of German Patent Application No. 10 2015 117 468.5, filed on Oct. 14, 2015 and International Patent Application No. PCT/EP2016/071198 filed on Sep. 8, 2016, the entire contents of which are incorporated herein by reference.

TECHNICAL FIELD

The present invention relates to a method for determining properties of a hydrocarbon containing gas mixture and to an apparatus therefor. The relevant gas mixtures are especially natural gas or biogas.

BACKGROUND

Natural gas is a fossil energy carrier. It has a composition dependent on where it came from in the ground. The main component of natural gas is methane, with a mol fraction of, for example, 75% to 99%. Frequently, natural gas also contains significant fractions of ethane (1% to 15%), propane (1% to 10%), butane and ethene. Other minor components are hydrogen sulfide, nitrogen, carbon dioxide and water vapor.

Biogas is a burnable gas mixture of different composition, which arises from fermentation of biomass of all kinds. It contains in the raw state especially methane (up to 60%) and carbon dioxide as main components. Other constituents are nitrogen, oxygen, hydrogen sulfide, water vapor and ammonia. Hydrogen sulfide and ammonia need to be removed before burning, or before feeding into the natural gas grid. Likewise, it is advantageous to remove the carbon dioxide before burning.

In order to be able to reliably control combustion processes, it is necessary rapidly to detect the current energy content of a gas mixture as it's being supplied to a process.

Patents DE 69 231 977 T2 and U.S. Pat. No. 5,311,447 A1 disclose methods for determining the energy content of a gas mixture from the thermal conductivity, the heat capacity, the optical absorption and the viscosity of the gas mixture.

A technically more relevant characterizing of the energy content is provided by the Wobbe index W, which is defined as the quotient of the energy content per unit volume H and the square root of the specific gravity. The specific gravity is the quotient of the density p of the burnable gas and the density of dry air $\rho_0$ under equal pressure- and temperature conditions:

$$W = \frac{H}{\sqrt{\frac{\rho}{\rho_0}}}$$

Gas mixtures with equal Wobbe index can be directly used interchangeably during operation of a burner.

The International Standard ISO 6976 establishes methods for calculating calorific value, heating value, density, specific gravity and Wobbe Index of dry natural gases, natural gas replacement gases and other combustible gases, when the composition of the gas is known in amount-of-substance fractions. This requirement is met in the normal case.

Publication GB 2,296,091 A describes a method for determining the calorific value, or the Wobbe index, of a gas mixture based on its thermal conductivity, density, viscosity, and velocity of sound. The firm, MEMS AG, offers a sensor with the designation, Gas QS, which determines calorific value and Wobbe index of a gas mixture based on its thermal conductivity, heat capacity and density.

The measuring of the above mentioned optical absorption or thermal parameters, such as thermal conductivity and heat capacity, are complex, however.

SUMMARY

There is, consequently, need for a simple, robust and reliable method and a corresponding measuring apparatus for determining properties of a gas mixture, especially its energy content, or Wobbe index. It is, therefore, an object of the present invention to provide such a method and such an apparatus.

The object of the invention is achieved by the method of independent claim 1 and the apparatus of independent claim 12.

The method of the invention for determining properties of a hydrocarbon containing gas mixture, especially natural gas or biogas, comprises:

allowing the gas mixture to flow through a measuring arrangement;

determining a pressure- and temperature dependent viscosity measured value, an associated measured value of temperature and an associated pressure measured value of the flowing gas mixture;

ascertaining a first value of a first variable, which characterizes the energy content of the flowing gas mixture, based on viscosity measured value, the associated measured value of temperature, and the associated pressure measured value, wherein the first variable characterizing the energy content is the Wobbe index or the calorific value of the flowing gas mixture, wherein the ascertaining of the first value of the first variable occurs especially based on a correlation calculation.

In a further development of the invention, the method additionally includes: determining a second value of a second variable, which characterizes the energy content of the flowing gas mixture, based on a current density measured value or a current velocity of sound measured value of the flowing gas mixture, at the associated pressure measurement value and the associated temperature measured value, without application of the viscosity measured value, wherein the second variable characterizing the energy content is the Wobbe index or the calorific value of the flowing gas mixture, wherein the ascertaining of the second value of the second variable occurs especially based on a correlation calculation.

In a further development of the invention, the method additionally includes:

either, to the extent that the first variable and the second variable are the same, ascertaining a deviation between the first value and the second value; and ascertaining the sum of the content of carbon dioxide and nitrogen based on the ascertained deviation, or, to the extent that the first variable and the second variable are different, converting the first value or the second value into a corresponding value of the other variable, ascertaining a deviation between the converted value, and the value present originally in the other characteristic variable; and ascertaining the sum of the content of carbon dioxide and nitrogen based on the ascertained deviation.

In a further development of the invention, the first variable is the Wobbe index of the flowing gas mixture.

According to this further development of the invention, the method for determining properties of a hydrocarbon containing gas mixture, especially natural gas or biogas, comprises: allowing the gas to flow through a measuring arrangement; determining a pressure- and temperature dependent viscosity measured value, an associated measured value of temperature and an associated pressure measured value of the flowing gas; and ascertaining the Wobbe index of the flowing gas based on viscosity measured value, the associated measured value of temperature, and the associated pressure measured value, wherein the ascertaining of the Wobbe index occurs especially based on a correlation calculation.

The Wobbe index is therefore preferably the first variable characterizing the energy content, because the correlation between the Wobbe index and the viscosity is better than the correlation between the calorific value and the viscosity.

In a further development of the invention, the second variable is the calorific value of the flowing gas mixture.

In a further development of the invention, the first value present as Wobbe index is converted into a calorific value, especially by multiplying the Wobbe index by the square root of the specific gravity of the gas mixture.

In this way, values ascertained from the viscosity for the Wobbe index and the calorific value can be provided, for example, for controlling the fuel gas supply to a burner or for ascertaining energy consumption.

In a further development of the invention, there precedes the ascertaining of a value of the Wobbe index as first variable the ascertaining of a standard viscosity value of the flowing gas mixture, which the flowing gas mixture would have at a standard temperature and a standard pressure, based on viscosity measured value, the associated measured value of temperature and the associated pressure measured value, wherein the ascertaining of the Wobbe index of the flowing gas mixture occurs based on the standard viscosity value of the gas mixture.

In a further development of the invention, firstly, the specific gravity of the gas mixture is determined based on a current density measured value or a current velocity of sound measured value of the gas mixture, and wherein then the second variable characterizing the energy content of the flowing gas mixture, especially the calorific value, is ascertained based on the specific gravity, wherein especially the specific gravity of the gas mixture is determined relative to dry air at standard temperature and standard pressure.

In a further development of the invention, the determining of viscosity and, in given cases, the density of the gas mixture occurs by means of a vibronic sensor, wherein the vibronic sensor is a MEMS sensor, which has at least one flowed through, oscillating, measuring tube and/or at least one oscillator, especially in the form of at least one oscillating cantilever or an oscillating tuning fork, surrounded by the flowing gas mixture.

In a further development of the invention, determining the velocity of sound occurs by means of travel time measurement between ultrasonic transducers.

The apparatus of the invention for determining properties of a hydrocarbon containing gas mixture, especially with the method of the invention, comprises:

a measuring arrangement, through which the gas mixture can flow, with a temperature sensor,
a pressure sensor and
a vibronic sensor for determining a viscosity measured value and, in given cases, a density measured value of the flowing gas mixture; and
an evaluating unit for calculating properties of the flowing gas mixture; wherein the properties include at least the Wobbe index of the gas.

In a further development of the invention, the vibronic sensor is a MEMS sensor, which has at least one through flowable, oscillatable measuring tube and/or at least one oscillator, especially in the form of at least one oscillatable cantilever or an oscillatable tuning fork, surrounded by the flowing gas mixture. A suitable MEMS sensor is described, for example, in Offenlegungsschrift DE 10 2014 115 566 A1.

In a further development of the invention, the apparatus includes at least one ultrasonic transducer for determining the velocity of sound of the flowing gas mixture.

BRIEF DESCRIPTION OF THE DRAWING

The invention will now be explained in greater detail based on the examples of embodiments illustrated in the drawing, the figures of which show as follows:

FIG. 3b shows a statistical analysis of the data of the correlation graph of FIG. 3a;

FIG. 5b shows a statistical analysis of the data of the correlation graph of FIG. 5a;

DETAILED DESCRIPTION

The invention is based on the statistical analysis of the physical properties of several thousand natural gas samples as a function of their composition. The composition was determined by means of gas chromatography. For the ascertained compositions, the physical properties of the gas mixtures were calculated at different pressure- and temperature values. Equally, the physical properties of some pure gases were calculated. For calculating the physical properties, a program of NIST was used, namely "Reference Fluid Thermodynamic and Transport Properties Database", REFPROP for short, version 9.1, which is accessible at the address http://www.nist.gov/srd/nist23.cfm. An experimental determining of the physical variables is equally possible, but such involves, however, a greater effort. The calculated physical variables include:

density: $\rho(T,p)$
specific gravity: $SG=\rho(T_{ref},p_{ref})/\rho_{air}(T_{ref},p_{ref})$
$SG_{ideal}(T,p): \rho(T,p)/\rho_{air}(T,p)$ Z-factor: $Z = \rho_{ideal}(T,p)/\rho_{real}(T,p)$
$= \rho(T,p)*(T/T_{ref})*(p_{ref}/p)/\rho(T_{ref},p_{ref})$ velocity, or speed, of sound SOS
dynamic viscosity: $\eta(T,p)$
calorific value: CV
Wobbe index: $WI=CV/\sqrt{SG}$ The development of the method of the invention performed based on the above data will now be explained in greater detail as follows.

Figure 1A:
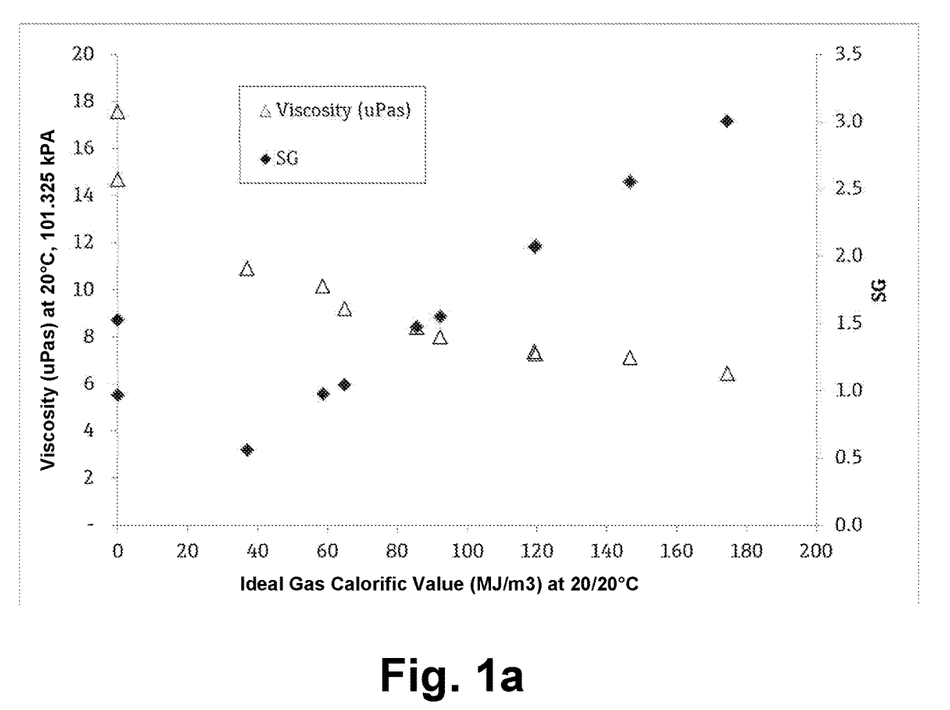
FIG. 1a shows a graph of viscosity and specific gravity of pure gases as a function of calorific value.

FIG. 1a shows dynamic viscosity and specific gravity of some pure gases versus their calorific values. The gases are methane, ethane, propane, n-butane, iso-butane, n-hexane, ethylene, propene, nitrogen and carbon dioxide. FIG. 1b shows again dynamic viscosity and, in contrast with FIG. 1a, velocity of sound of the same gases versus their calorific values. The gases are methane, ethane, propane, n-butane, iso-butane, n-hexane, ethylene, propene, nitrogen and carbon dioxide. Both graphs indicate a usable correlation between the dynamic viscosity and the calorific value of the gases. Specific gravity and velocity of sound likewise have a noticeable correlation with the calorific value of the pure burnable gases, but, in the case of nitrogen and carbon dioxide, such correlation is not present. This leads to the idea of determining the fraction of nitrogen and carbon dioxide in a gas mixture, as will be developed in a while below. First, however, determining of the Wobbe index and the calorific value will be explored.

Figure 1B:
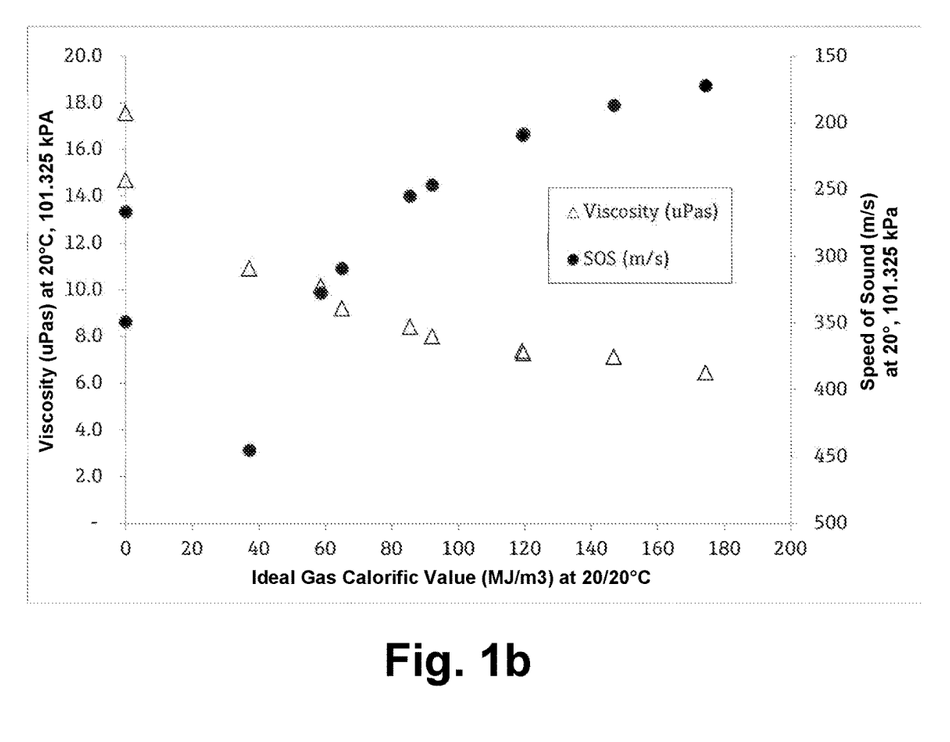
FIG. 1b shows a graph of viscosity and velocity of sound of pure gases as a function of calorific value.
Figure 2A:
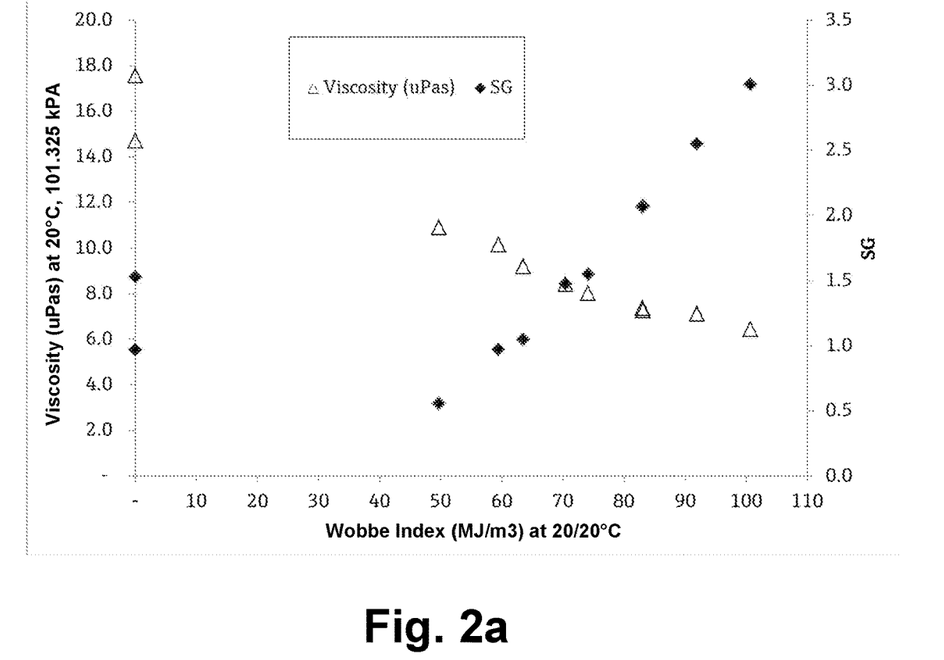
FIG. 2a shows a graph of viscosity and specific gravity of pure gases as a function of Wobbe index.

FIG. 2a shows dynamic viscosity and specific gravity of the same gases as in FIGS. 1a and 1b versus their Wobbe index. With knowledge of FIGS. 1a and 1b, it is not surprising that the viscosity, again, shows a usable correlation with the Wobbe index of all analyzed gases, while the correlation between the specific gravity and the Wobbe index of pure gases cannot be extrapolated to carbon dioxide and nitrogen.

Figure 2B:
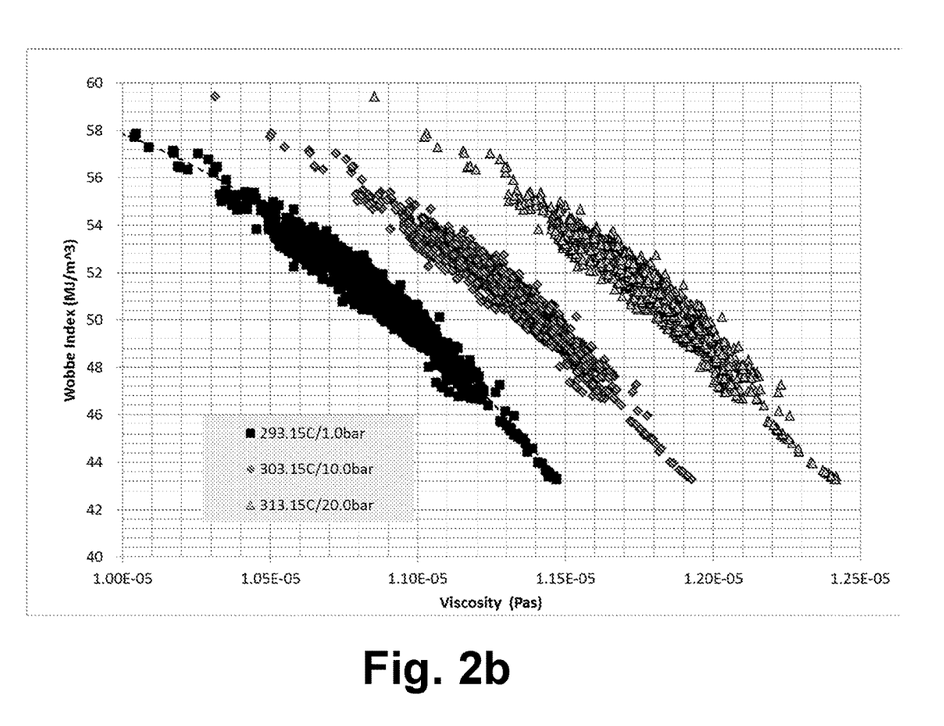
FIG. 2b shows a graph of Wobbe index of various gas mixtures as a function of viscosity at different temperatures and pressure values.

The correlation between Wobbe index and dynamic viscosity provides a basis for determining the Wobbe index based on viscosity, as is shown in FIG. 2b for gas mixtures at different pressure- and temperature values. The Wobbe index is, for example, representable as a polynomial of the viscosity, wherein the coefficients of the polynomial have a pressure- and temperature dependence. The polynomial should preferably be at least second degree, wherein currently a polynomial of third degree is preferable. Fundamentally, however, also polynomials of higher order are possible for determining the Wobbe index, for example, fourth, fifth or sixth order. For implementing the method of the invention, the pressure- and temperature dependence of the coefficients are determined, in order, based on a viscosity value of a gas mixture at a pressure- and temperature value, to determine the Wobbe index.

Equally, from a current viscosity value $\eta(T,p)$ at a given pressure p and a given temperature T, firstly, a viscosity can be determined at reference conditions $\eta(STP)$, and then the Wobbe index calculated based on viscosity at reference conditions. The viscosity at reference conditions $\eta(STP)$ is calculated from a current viscosity value, for example, using the formula:

$\eta(STP)=\eta(T,p)/C_\eta$

In such case, the compensation factor $C_\eta$ is a function of pressure and temperature, determined, for example, in the following way:

$C_\eta=C_0(SG)+C_1(SG)\cdot p+C_2(SG)\cdot T$ $C_0(SG)=a_1*SG^2+b_1*SG+c_1$ $C_1(SG)=a_2*SG^2+b_2*SG+c_2$ $C_2(SG)=a_3*SG^2+b_3*SG+c_3$ In such case, $a_i$, $b_i$, $c_i$ (i=1, 2, 3) are coefficients, which depend on the specific gravity SG of the gas mixture. For the present invention, the coefficients for the compensation factors were determined based on the properties of more than six thousand natural gas samples over a temperature range between 20° C. and 40° C. and a pressure range between 1 and 20 bar. The standard error of the compensation factor amounts here to less than 0.1% and the maximum error to less than 0.8%.

Figure 3A:
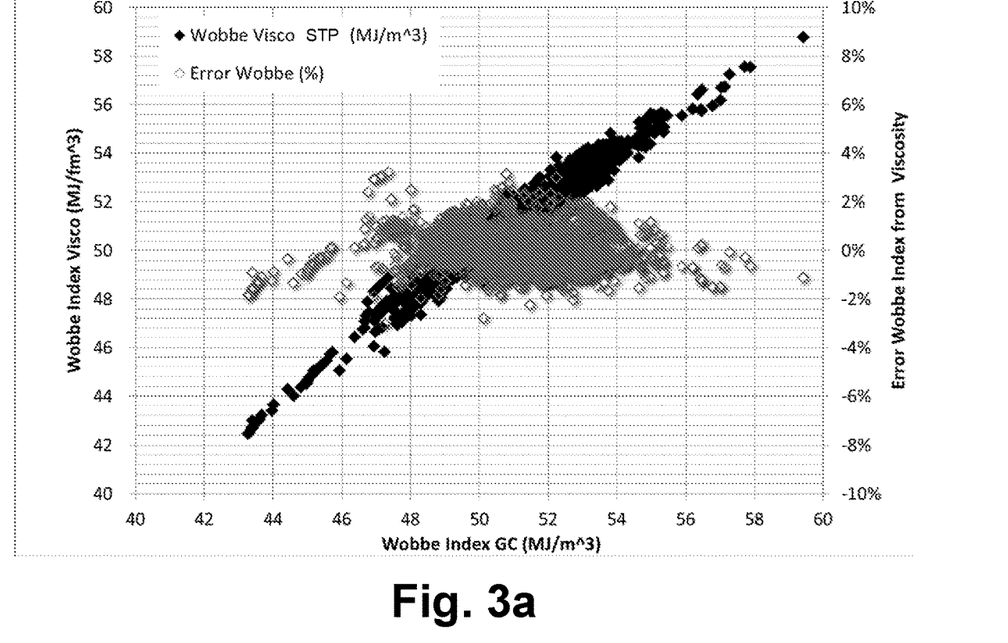
FIG. 3a shows a correlation graph for the Wobbe index determined by means of the method of the invention versus the Wobbe index based on the actual composition of gas mixtures.
Figure 3B:
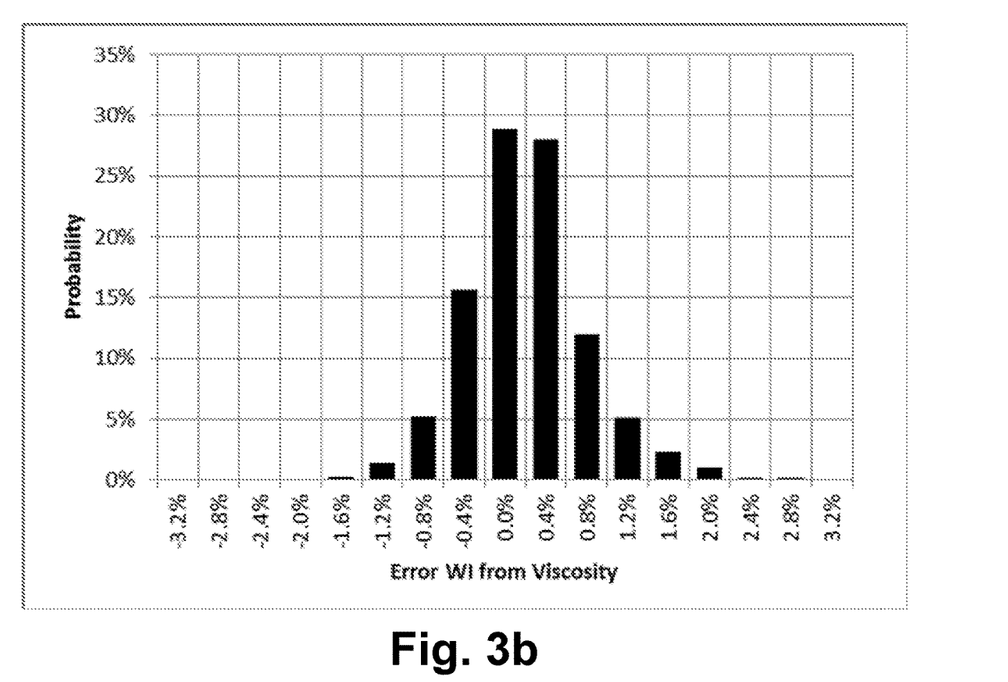

FIG. 3a shows Wobbe index ascertained with the method of the invention based on viscosity at standard conditions $\eta(STP)$ versus actual Wobbe index for thousands of natural gas samples, wherein the viscosity at standard conditions $\eta(STP)$ was ascertained based on the above model from a viscosity $\eta(T,p)$ at other pressure and temperature values. Additionally shown is the relative error of the Wobbe index of the invention with reference to the actual Wobbe index. A distribution of the relative error of the Wobbe index determined according to the invention relative to the actual Wobbe index is shown in FIG. 3b. In accordance therewith, the 3σ interval of the Wobbe index error based on the method of the invention amounts to, for instance, ±3%. This is a sufficiently good result, in order to characterize with the method of the invention a burnable gas supplied, for example, to a burner.

Figure 4A:
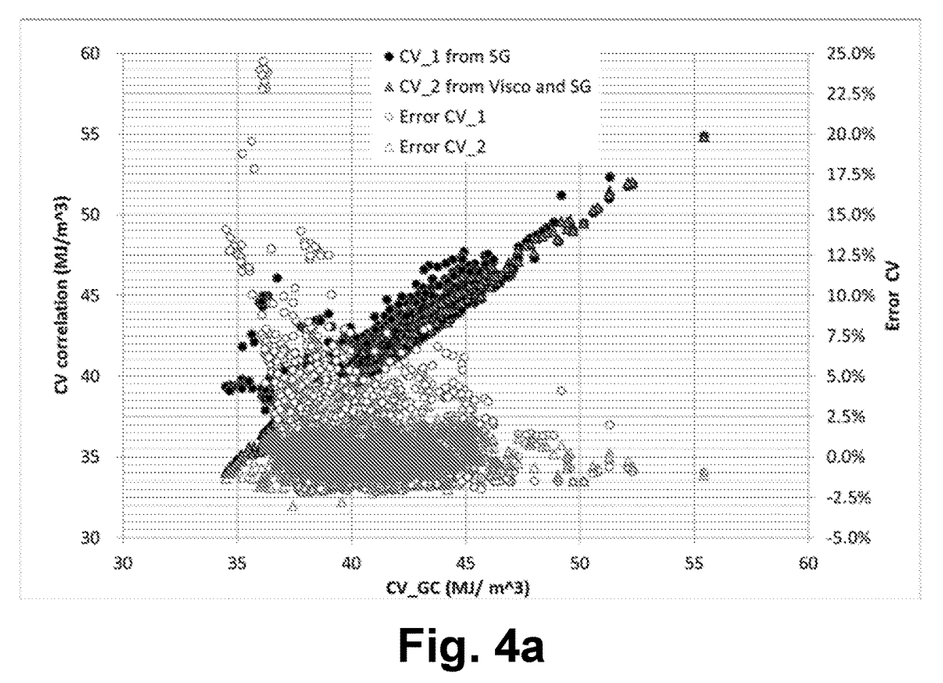
FIG. 4a shows a correlation graph for calorific values ascertained by means of correlation calculation with and without taking the viscosity value into consideration versus actual calorific value based on the composition of gas mixtures.

From the Wobbe index of a gas mixture ascertained according to the invention based on a viscosity measurement, the calorific value of the gas mixture can be determined by multiplication with the square root of its specific gravity. On the other hand, the calorific value of a gas mixture exhibits a good correlation with its specific gravity, provided that the inert gases nitrogen and carbon dioxide play no role. If these components are present, the correlation no longer holds. This situation is presented in FIG. 4a. FIG. 4a shows gas mixture calorific values ascertained by means of the above correlation methods plotted versus the actual calorific values. Equally shown are the relative errors with reference to actual calorific value. The graph shows that the two correlation methods in the case of high calorific values deliver results agreeing quite well and largely correct, and that, in the case of low calorific values, which, usually, means significant nitrogen and carbon dioxide, or inert, gas, fractions, the correlation calculation only based on the specific gravity without taking into consideration the viscosity delivers deviating and incorrect results for the calorific value. Error above 20% occurs. As already indicated in connection with FIG. 1a, an opportunity is provided for turning necessity into a virtue. This will now be explained based on FIG. 4b.

Figure 4B:
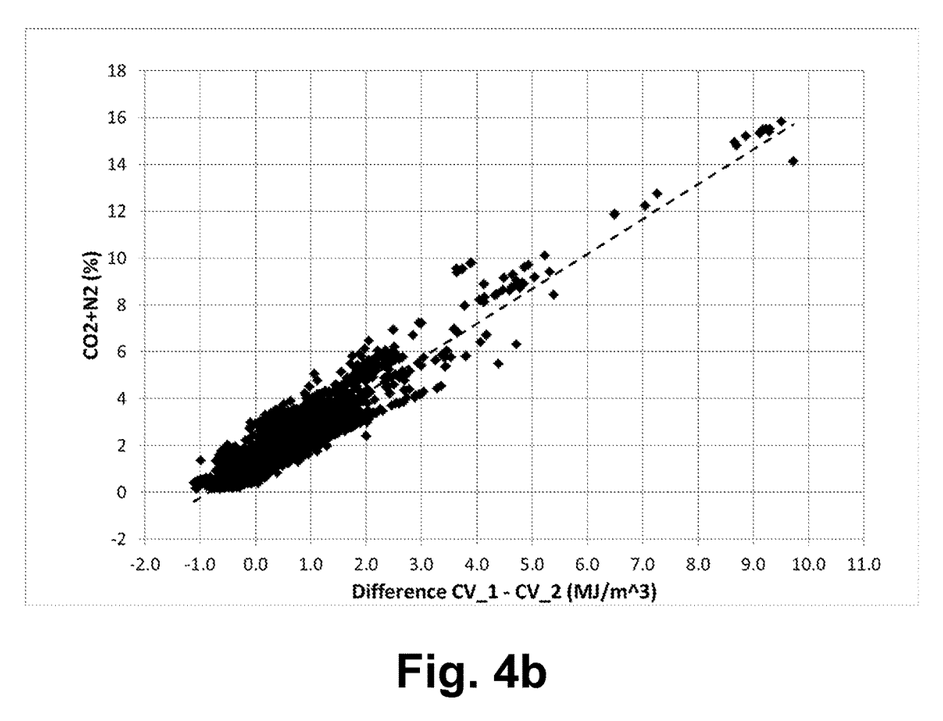
FIG. 4b shows a correlation graph of the actual content of carbon dioxide and nitrogen of various gas mixtures versus the difference between the calorific values ascertained by means of correlation calculation taking the viscosity value into consideration and the calorific values ascertained by means of correlation calculation without taking the viscosity value into consideration.

FIG. 4b shows the actual inert gas fraction of the several thousand investigated natural gas samples versus the difference between a calorific value ascertained only by correlation calculation and a second calorific value ascertained by correlation calculation, wherein the first calorific value was ascertained only based on the specific gravity without taking the viscosity into consideration, and wherein the second calorific value was ascertained via the viscosity dependent Wobbe index and the specific gravity. The inert gas fraction shows a usable correlation with above calorific value difference. In accordance therewith, the inert gas fraction can be determined as a function of calorific value difference by means of correlation calculation. The accuracy that this approach actually contributes for determining the inert gas fraction is evident based on FIGS. 5a and 5b.

Figure 5A:
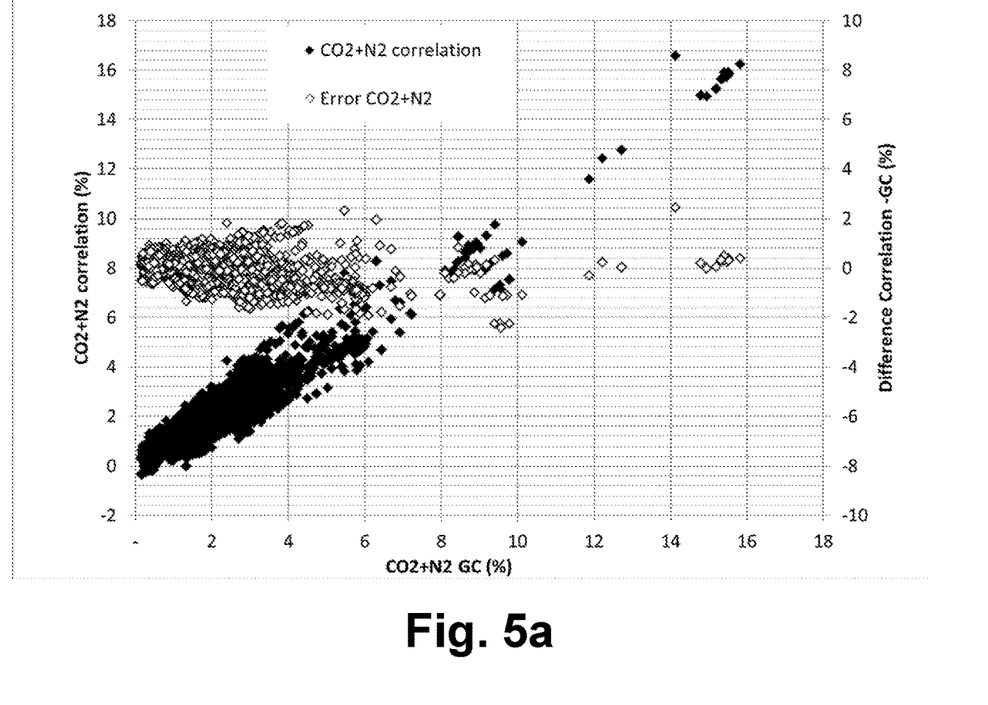
FIG. 5a shows a correlation graph for the content of carbon dioxide and nitrogen ascertained by means of the method of the invention versus the actual content of carbon dioxide and nitrogen of gas mixtures.
Figure 5B:
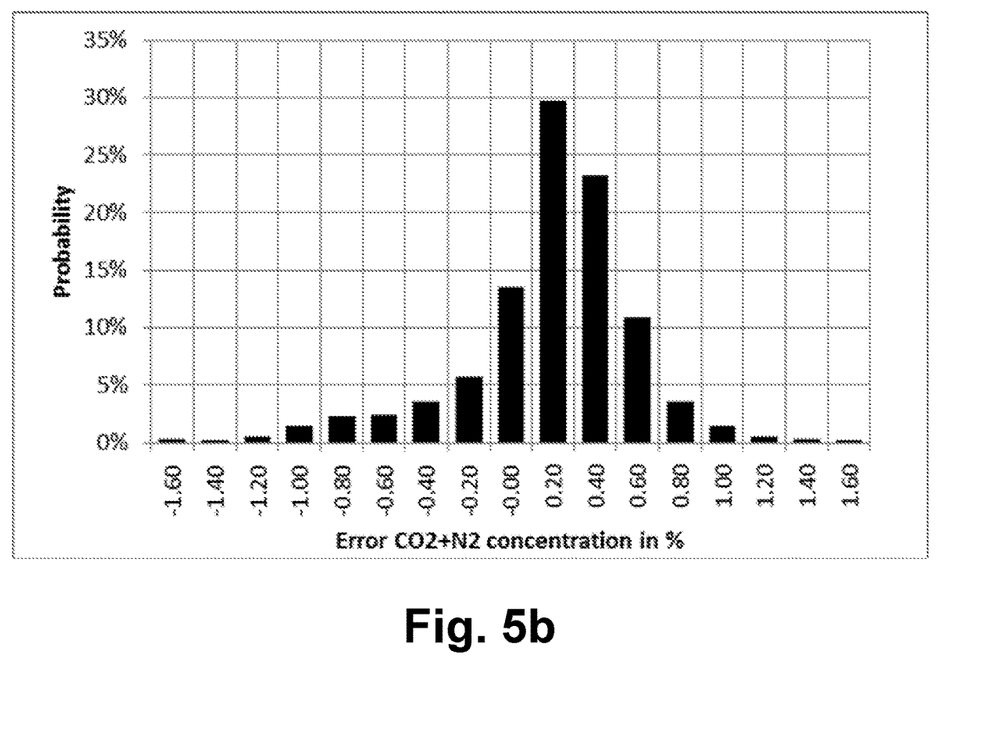

FIG. 5a shows the inert gas fraction determined according to the invention by means of correlation calculation as a function of calorific value difference versus the actual inert gas fraction of the several thousand investigated natural gas samples determined by means of gas chromatography. It shows excellent agreement. A statistical evaluation of the deviation between the inert gas fraction determined according to the invention and the actual inert gas fraction is presented in FIG. 5b. The error of the inert gas content has accordingly a 3σ-value of, for instance, ±1.5%. This is sufficient accuracy for the analysis of a burnable gas, for example, in the case of burner control.

Figure 6A:
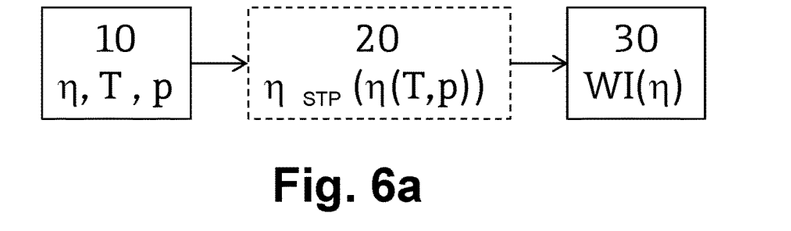
FIG. 6a shows a flow diagram of a first example of an embodiment of the method of the invention.
Figure 6B:
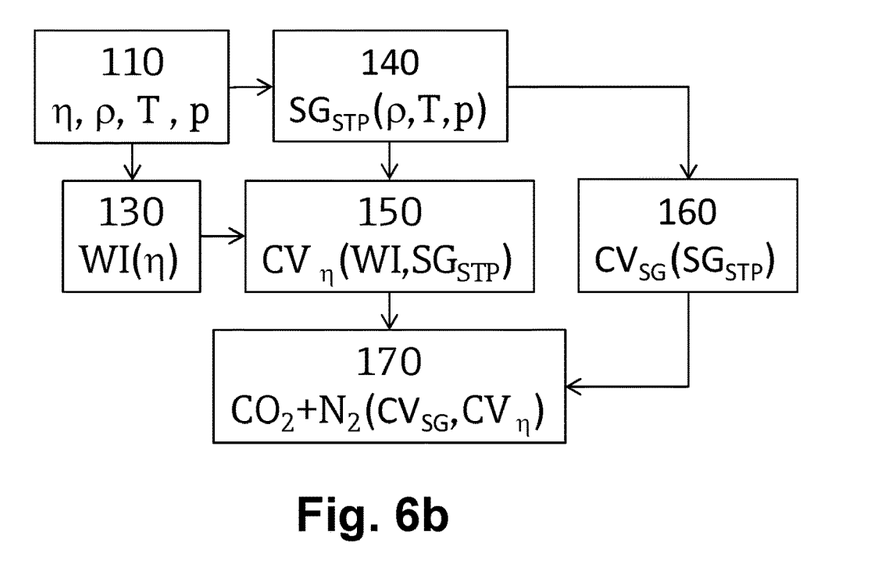
FIG. 6b shows a flow diagram of a second example of an embodiment of the method of the invention.
Figure 6C:
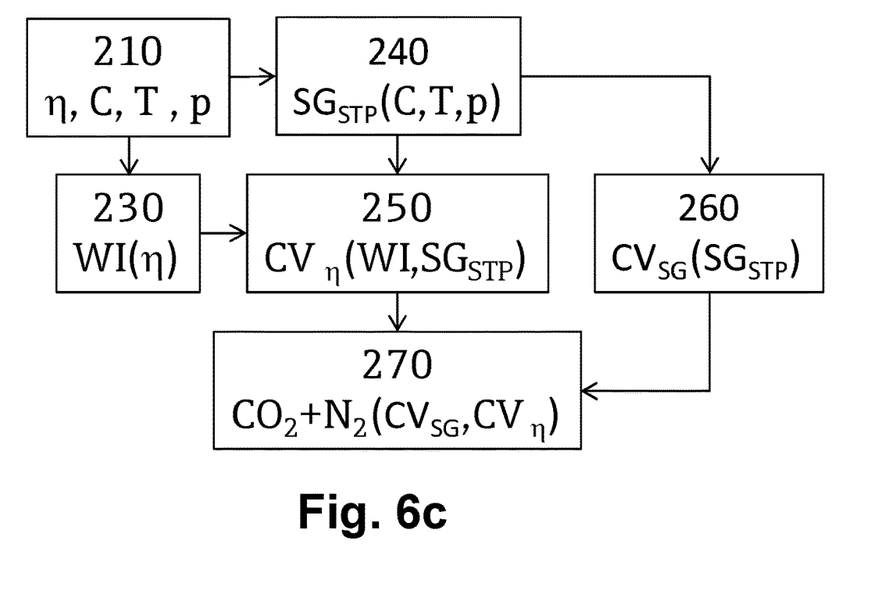
FIG. 6c shows a flow diagram of a second example of an embodiment of the method of the invention.

To summarize, FIGS. 6a to 6c show flow diagrams of examples of embodiments of the method of the invention.

The example of an embodiment of the method of the invention shown in FIG. 6a includes in a step 10 the registering of a viscosity measured value η, a measured value of temperature T and a pressure measured value p of the flowing gas mixture, wherein the named measured values are to be registered as simultaneously as possible and the sensors required therefor are to be arranged preferably as near as possible to one another, so that the measured values form a value tuple of the gas mixture in a thermodynamic state. The measuring of the viscosity occurs, for example, with a vibronic sensor, especially an oscillating cantilever, which is surrounded by the gas mixture. Optionally, in a step 20, firstly, a viscosity measured value at standard conditions can be determined from the current viscosity measured value at a given pressure p and a given temperature T. Finally in a step 30, based on a viscosity value, be it the directly measured viscosity measured value or the viscosity at standard conditions, the Wobbe index of the gas mixture is determined, such as was explained above in connection with FIG. 2b.

The example of an embodiment of the method of the invention shown in FIG. 6b includes in a step 110 the registering of a viscosity measured value η, a density measured value ρ, a measured value of temperature T and a pressure measured value p of the flowing gas mixture. The same conditions as in the case of the first example of an embodiment hold for the measured value registering. The density of the gas mixture can likewise be determined with the vibronic sensor, since its resonant frequency depends on the density.

In a step 130, based on a viscosity value, be it the directly measured viscosity measured value or a viscosity derived therefrom at standard conditions, the Wobbe index of the gas mixture is determined. In a step 140, from the density measured value, as well as the associated pressure- and temperature measured values, the specific gravity SG of the gas mixture is determined. From the specific gravity and the viscosity dependent Wobbe index, in a step 150, a first value $CV_\eta$ for the calorific value is ascertained. Furthermore, in a step 160, only based on the specific gravity, which correlates with the calorific value, as long as no inert gases are present, such as was explained based on FIG. 1a, a second value for the calorific value of the gas mixture is ascertained. From the difference between the first value for the calorific value of the gas mixture and the second value for the calorific value of the gas mixture, the inert gas fraction is determined, as is shown in FIG. 4b.

The example of an embodiment of the method of the invention shown in FIG. 6c includes in a step 210 the registering of a viscosity measured value η, a value for the velocity of sound C, a measured value of temperature T and a pressure measured value p of the flowing gas mixture. The same conditions as in the case of the first example of an embodiment hold for the measured value registering. The velocity of sound C can be determined, for example, with two ultrasonic transducers of, for example, a flow measuring device, which registers a flow rate of the flowing gas mixture.

In a step 230, based on a viscosity value, be it the directly measured viscosity measured value or a viscosity at standard conditions as derived therefrom, the Wobbe index of the gas mixture is determined. In a step 240, from the velocity of sound, as well as the associated pressure- and temperature measured values, the specific gravity SG of the gas mixture is determined. From the specific gravity and the viscosity dependent Wobbe index, in a step 250, a first value $CV_\eta$ for the calorific value is ascertained. Furthermore, in a step 260, only based on the specific gravity, which correlates with the calorific value, as long as no inert gases are present, such as was explained based on FIG. 1a, a second value for the calorific value of the gas mixture is ascertained. From the difference between the first value for the calorific value of the gas mixture and the second value for the calorific value of the gas mixture, the inert gas fraction in determined, as is shown in FIG. 4b.

The method of the invention operates further under the assumption that the flowing gas contains little, if any, molecular hydrogen, which would also contribute to the calorific value, at most, at low concentration, for example, no greater than 1%, especially no greater than 0.1%. This assumption is justified for natural gas and biogas. When the burnable gas contains higher hydrogen fractions, this leads correspondingly to systematic errors.

Figure 7:
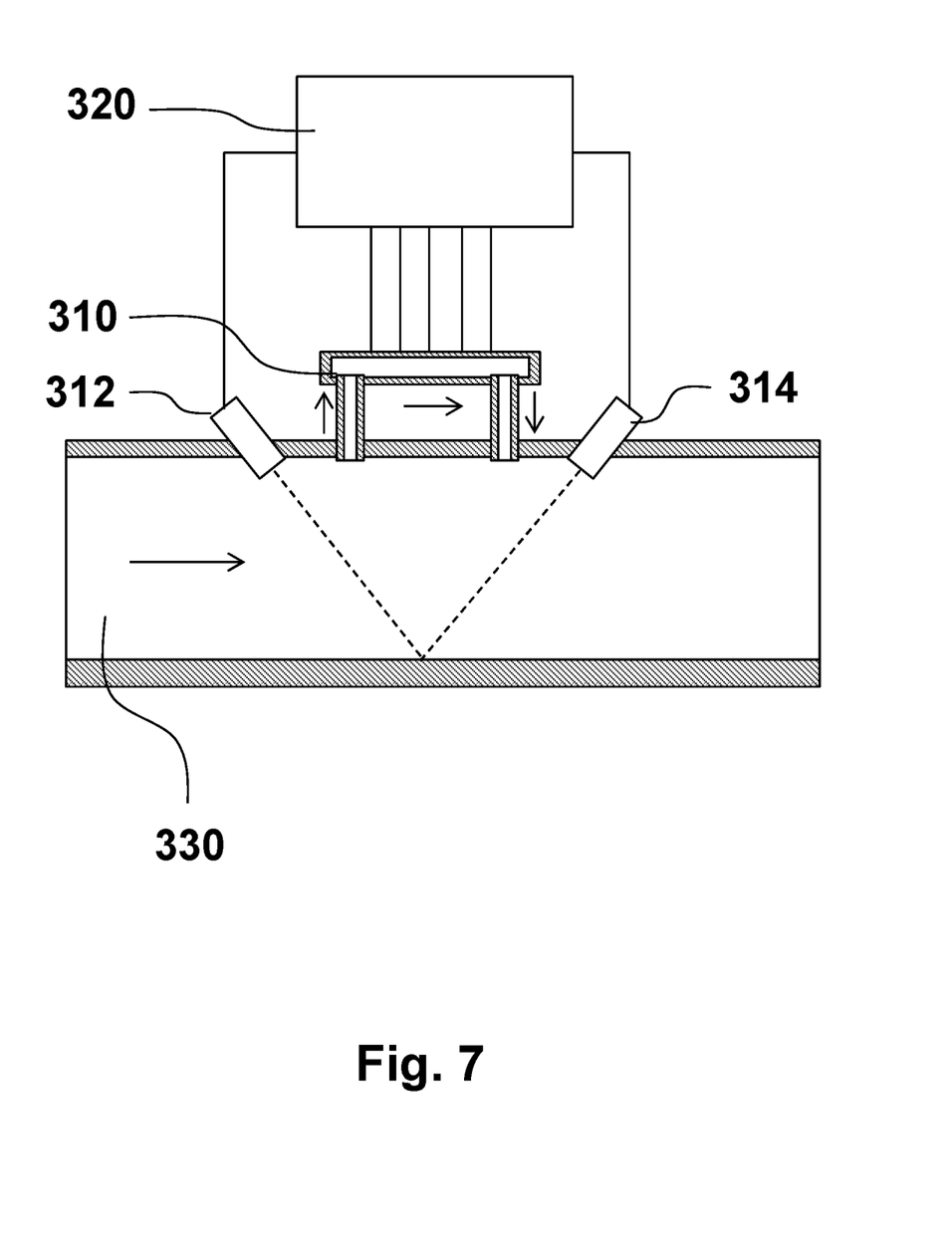
FIG. 7 shows an example of an embodiment of an apparatus for performing the method of the invention.

The example of an embodiment of an apparatus of the invention shown in FIG. 7 for performing the method of the invention includes a measuring cell 310, through which the gas mixture can flow and in which are arranged sensor elements (not shown), namely a cantilever oscillator for determining viscosity and, in given cases, the density of a gas mixture in the measuring cell, a pressure sensor and a temperature sensor. The sensor elements are preferably implemented in MEMS technology. The apparatus further comprises an operating- and evaluation unit 320 for operating the sensor elements, for evaluating their signals, in order to determine the primary measured variables, such as viscosity, pressure, temperature and, in given cases, density, and for ascertaining the Wobbe index and/or the calorific value and/or the inert gas fraction of a gas mixture flowing through the measuring cell 310. The operating- and evaluation unit comprises for this a computing unit, which can be compactly or modularly constructed, and especially can include modules spatially separated from one another. The measuring cell 310 is especially connected as a bypass of a gasline 330, wherein a volume flow rate of the gas mixture can be driven through the measuring cell 310 by means of a pressure difference along the measuring cell 310, for example, due to a diaphragm, or a Venturi nozzle, in the pipeline, or by means of a pump (not shown).

The apparatus can, furthermore, have two ultrasonic transducers 312, which, for example, are connected to the gasline 330, in order to determine, for example, using the travel time difference method, volume flow through the gasline and the velocity of sound in the flowing gas mixture.

The invention claimed is:

1. A method for determining properties of a hydrocarbon-containing gas mixture, comprising:
   flowing the gas mixture through a measuring arrangement;
   measuring a pressure- and temperature-dependent viscosity, an associated temperature, and an associated pressure of the gas mixture; and
   calculating a first value of a first variable based on the pressure- and temperature-dependent viscosity, the associated temperature, and the associated pressure, wherein the first variable characterizes the energy content of the gas mixture and is a Wobbe index or a calorific value of the gas mixture;
   measuring at least one of a current density of the gas mixture and a current velocity of sound in the gas mixture;
   calculating a second value of a second variable based on the current density or the current velocity of sound, at the associated pressure and the associated temperature, without application of the pressure- and temperature-dependent viscosity, wherein the second variable characterizes the energy content of the gas mixture and is the Wobbe index or the calorific value of the gas mixture;
   wherein the first variable and the second variable are the same parameter;
   when values of the first variable and the second variable are the same, calculating a deviation between the first value and the second value and calculating a sum of the content of carbon dioxide and nitrogen in the gas mixture based on the calculated deviation; or
   when values of the first variable and the second variable are different, converting the first value or the second value into a corresponding value of the other variable;
   calculating a deviation between the corresponding value and the value of the other variable; and calculating a sum of the content of carbon dioxide and nitrogen in the gas mixture based on the calculated deviation.

2. The method as claimed in claim 1,
   wherein the first value of the first variable is the Wobbe index of the gas mixture,
   wherein the second value of the second variable is the calorific value of the gas mixture, and
   wherein the first value of the first variable is converted into a calorific value.

3. The method as claimed in claim 1, further comprising:
   before calculating the second value, calculating a specific gravity of the gas mixture based on the current density or the current velocity of sound; and
   calculating the second value based on the specific gravity.

4. The method as claimed in claim 3, wherein the specific gravity of the gas mixture is calculated relative to dry air at standard temperature and standard pressure.

5. The method as claimed in claim 1, wherein the measuring arrangement includes a vibronic sensor, and wherein the measuring of pressure- and temperature-dependent viscosity and of the current density of the gas mixture occurs using the vibronic sensor.

6. The method of claim 5, wherein the vibronic sensor is a MEMS sensor having at least one flowed-through, oscillating, measuring tube and/or at least one oscillator in the form of an oscillating cantilever or an oscillating tuning fork and surrounded by the gas mixture.

7. The method as claimed in claim 1, wherein the measuring arrangement includes two ultrasonic transducers, and wherein the measuring of the current velocity of sound includes measuring a travel time of sound waves between the two ultrasonic transducers.

8. The method as claimed in claim 1, further comprising:
   before calculating the first value, calculating a standard viscosity of the gas mixture based on the pressure- and temperature-dependent viscosity, the associated temperature, and the associated pressure, wherein the standard viscosity is a viscosity the gas mixture would have at a standard temperature and a standard pressure; and
   calculating the Wobbe index of the gas mixture based on the standard viscosity.

9. An apparatus for determining properties of a hydrocarbon-containing gas mixture, comprising:
   a measuring arrangement including
      a temperature sensor,
      a pressure sensor, and
      a vibronic sensor embodied to determine a viscosity of the gas mixture and a density of the gas mixture; and
   an evaluating unit configured to calculate at least the Wobbe index of the gas mixture and the calorific value of the gas mixture,
   wherein the measuring arrangement is configured to enable the gas mixture to flow through the measuring arrangement wherein:
   the apparatus is configured to perform a method for determining properties of a hydrocarbon-containing gas mixture, comprising:
   flowing the gas mixture through a measuring arrangement;
   measuring a pressure- and temperature-dependent viscosity, an associated temperature, and an associated pressure of the gas mixture; and
   calculating a first value of a first variable based on the pressure- and temperature-dependent viscosity, the associated temperature, and the associated pressure, wherein the first variable characterizes the energy content of the gas mixture and is a Wobbe index or a calorific value of the gas mixture,
   measuring at least one of a current density of the gas mixture and a current velocity of sound in the gas mixture;
   calculating a second value of a second variable based on the current density or the current velocity of sound, at the associated pressure and the associated temperature, without application of the pressure- and temperature-dependent viscosity, wherein the second variable characterizes the energy content of the gas mixture and is the Wobbe index or the calorific value of the gas mixture;

wherein the first variable and the second variable are the same parameter;

when values of the first variable and the second variable are the same,
- calculating a deviation between the first value and the second value and calculating a sum of the content of carbon dioxide and nitrogen in the gas mixture based on the calculated deviation; or when the values of the first variable and the second variable are different, converting the first value or the second value into a corresponding value of the other variable, calculating a deviation between the corresponding values and the value of the other variable, and calculating a sum of the content of carbon dioxide and nitrogen in the gas mixture based on the calculated deviation.

10. The apparatus as claimed in claim 9, wherein the vibronic sensor is a MEMS sensor having at least one through flowable, oscillatable measuring tube and/or at least one oscillator surrounded by the gas mixture, wherein the at least one oscillator is an oscillatable cantilever or an oscillatable tuning fork.

11. The apparatus as claimed in claim 9, further comprising at least one ultrasonic transducer embodied to determine the velocity of sound in the gas mixture.

* * * * *